United States Patent [19]

Venturello et al.

[11] Patent Number: 5,179,205
[45] Date of Patent: Jan. 12, 1993

[54] HETEROCYCLIC PEROXIDES HAVING N-AMIDIC HETEROATOMS

[75] Inventors: Carlo Venturello, Novara; Claudio Cavalotti, Milan, both of Italy

[73] Assignee: Ausimont S.r.l., Milan, Italy

[21] Appl. No.: 687,147

[22] Filed: Apr. 18, 1991

Related U.S. Application Data

[62] Division of Ser. No. 366,512, Jun. 14, 1989, Pat. No. 5,041,546.

[30] Foreign Application Priority Data

Jun. 14, 1988 [IT] Italy .................. 20957 A/88

[51] Int. Cl.⁵ .................. C07D 211/36; C07D 211/42; C07D 211/44; D06L 3/00
[52] U.S. Cl. .................. 546/189; 540/596; 540/597; 540/602; 548/518; 548/519; 548/520; 252/95; 546/188
[58] Field of Search ................ 546/189, 188; 540/484, 540/597, 602, 596; 548/518, 519, 531, 520; 252/95

[56] References Cited

U.S. PATENT DOCUMENTS

| | | | |
|---|---|---|---|
| 4,681,592 | 7/1987 | Hardy et al. | 560/129 |
| 4,686,063 | 8/1987 | Burns | 252/102 |
| 4,822,883 | 4/1989 | Myers | 546/16 |
| 4,994,573 | 2/1991 | Venturello | 546/318 |

OTHER PUBLICATIONS

"The Vocabulary of Organic Chemistry", Orchin et al, John Wiley & Sons p. 98.

Primary Examiner—C. Warren Ivy
Assistant Examiner—Celia Chang
Attorney, Agent, or Firm—Morgan & Finnegan

[57] ABSTRACT

Heterocyclic (poly)peroxycarboxylic acids having a N-amidic heteroatom, which have the formula:

$$R-(CH_2)_m-R' \quad (I)$$

wherein: R and R', alike or different from each other, represent hydrogen atoms or a group:

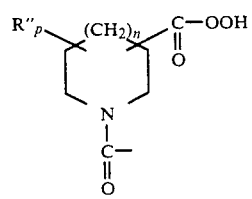

with the proviso that at least one of R and R' shall be different from H, and wherein the other symbols have the following meaning:

R'' represents a hydrogen atom or any other substituent non-reactive in the presence of the active oxygen of the peroxycarboxylic group and/or under the preparation conditions;

m represents a number between 1 to 12;

n represents a number selected from 0, 1 and 2;

p represents a number between 1 and 3;

their process of preparation and their use as bleaching agents.

5 Claims, No Drawings

HETEROCYCLIC PEROXIDES HAVING N-AMIDIC HETEROATOMS

This is a divisional of co-pending application Ser. No. 07/366,512 filed Jun. 14, 1989, now U.S. Pat. No. 5,041,546.

The present invention relates to per se new organic (poly)peroxyacids which may be referred to as heterocyclic (poly)peroxycarboxylic acids having N-amidic heteroatoms, and to the relevant preparation process.

More particularly, the present invention relates to heterocyclic (poly)peroxycarboxylic acids having a nitrogen amidic heteroatom having the formula:

$$R-(CH_2)_m-R' \qquad (I)$$

wherein: R and R', alike or different from each other, represent hydrogen atoms or a group:

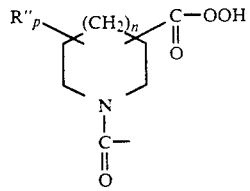

with the proviso that at least one of R and R' shall be different from H, and wherein the other symbols have the following meanings:

R" represents a hydrogen atom or any other substituent nonreactive in the presence of the active oxygen of the peroxycarboxylic group and/or under the preparation conditions;

m represents a number between 1 to 12;

n represents a number selected from 0, 1 and 2;

p represents a number between 1 and 3;

to their preparable process, and to their use as bleaching agents.

The heterocyclic peroxycarboxylic compounds having the above formula (I) are per se novel, and constitute a new class of highly interesting products from an industrial viewpoint.

They, in fact, may find a general use, similarly to those already known for peroxyacids, in the field of plastics as monomer polymerization initiator agents, and, in particular, as oxidizing agents for olefin epoxidation or hydroxylation, and in many other oxidative processes in the field of fine chemistry.

More specifically, however, the heterocyclic (poly)-peroxycarboxylic acids having an amidic nitrogen atom having the above formula (I), find a particularly efficacious application in the field of bleaching, in the detergent industry.

In past years organic peroxyacids aroused an increasing interest in the industrial field, due to their excellent possibilities for use as bleaching agents in compositions for medium-low temperature washing, more widespread also due to energy saving considerations.

Therefore considerable research activity exists aiming at finding organic peroxyacid compounds endowed with the necessary requisites of bleaching activity, thermal stability, and storage stability or shelf life.

Therefore many either mono- or di-peroxycarboxylic, straight or cyclic, organic peroxyacids are known and used, among others, in the detergent field.

Previously described peroxycarboxylic acids are, e.g., diperoxydodecanedioic acid, monoperoxyphthalic acid, diperazelaic acid and substituted diperoxyglutaric and adipic acids, and finally acylamino-(alkyl)-arylen-peroxycarboxylic acids, which however, are not included in the class of heterocyclic peroxycarboxylic acids having an N-amidic heteroatom which forms the subject matter of the present invention.

An object of the present invention is to provide, as per se novel compounds, a class of heterocyclic (poly)-peroxycarboxylic acids having an N-amidic heteroatom as in the above formula (I).

Another object of the present invention is to provide a simple and cheap process for the preparation of the above peroxycarboxylic acids having the above formula (I).

A still further object of the present invention is the use of the heterocyclic peroxycarboxylic acids having the above formula (I) as bleaching agents in detergent formulations, and particularly, in those destined for low-medium temperature use.

These and still other objects of the invention are achieved, according to the present invention, by the provision of nitrogen-containing heterocyclic peroxycarboxylic acids having the above formula (I), and by the relevant preparation process. They are obtained by substantially conventional methods. For example, they are obtained by the reaction of a substrate constituted by the heterocyclic (poly)carboxylic acids having the amidic nitrogen heteroatom (having the structure corresponding to the desired peracid of formula (I)) with $H_2O_2$ in concentrated methanesulphonic acid, and subsequent separation, etc., according to known techniques.

In this way, the peroxycarboxylic acids having the formula (I) are obtained as stable solids.

Defined in a more explicit way, the process according to the present invention consists or consists essentially in the peroxycarboxylation reaction with $H_2O_2$ of the substrate corresponding to the desired acid of formula (I) in an acid medium, for example a medium constituted by methanesulphonic acid.

The thus-obtained product is then filtered, extracted with solvent (methylene chloride, etc.), dried, and so forth, according to per se known techniques.

As stated above, the substrate used as the starting material is constituted in the N-amidic heteroatom-containing heterocyclic (poly)peroxycarboxylic acid corresponding to the desired (poly)peroxycarboxy acid of formula (I). The starting compounds are per se known and/or may be prepared according to conventional techniques.

Referring to the above formula (I), R" is particularly constituted by a hydrogen atom or by an alkyl, cycloalkyl, alkyl-aryl or aryl-aryl group containing an overall number of up to 10 carbon atoms. Such groups may in turn be substituted with one or more atoms or groups, either alike or different from one another, inert under the reaction conditions under which the preparation takes place, such as, e.g., F, Cl, $NO_2$, lower $C_1$-$C_5$ alkoxy group, and so forth.

As an alternative, R" is constituted by any other substituent group which does not react with the active oxygen of the peroxycarboxylic group, e.g., a carboxylic group, an F atom, a Cl atom, an $NO_2$ group, a lower $(C_1$-$C_5)$-alkoxy groups, and so forth.

The number n is preferably 1 when R is hydrogen.

Suitable substrates have proved to be, as examples, N-acetyl-4-piperidine carboxylic acid; N-decanoyl-4-piperidine carboxylic acid; N-N'-adipoyl-bis (4-piperidinecarboxylic) acid; N-decanoyl-3-piperidinecarboxylic acid; N, N'-succinyl-bis (3-piperidinecarboxylic) acid; N, N'-glutaryl-bis (3-piperidinecarboxylic) acid; N-hexanoyl-4-piperidinecarboxylic acid; N-decanoyl-6 methyl-4-piperidine carboxylic acid.

In case R"=COOH, preferably in a non-orthoposition with respect to the nitrogen atoms, the peroxycarboxylation of R" may also be carried out, thus obtaining a product of formula (I) with two or more peroxycarboxylic groups.

In case of the presence of two adjacent carboxylic groups (R'=COOH) the corresponding anhydride may also be used.

According to a preferred operating mode using methanesulphonic acid, the peroxycarboxylation reaction of the acid or poly-acid, used as the starting substrate, is carried out by gradually adding $H_2O_2$, having a concentration within the range of from approximately 70% to approximately 90% by weight, to a solution of the substrate in $CH_3SO_3H$ by maintaining the reaction temperature throughout the course of the reaction at a value of at least equal to 0° C., and preferably between approximately 10° and 30° C., depending on the reactivity of the substrate.

The amount of $CH_3SO_3H$, determined at a concentration of 100%, is at least 5 moles per each mole of substrate, and normally it is 8 and 30 moles per each mole of substrate, and is preferably between approximately 10 and 14 moles.

The hydrogen peroxide is used in an amount which is in excess at least equal to 2 moles per each mole of substrate, and usually is between 3 and 10 moles per each mole of substrate, and preferably between 4 and 6 moles per each mole of substrate, according to the COOH groups to be percarboxylated.

The reaction time depends on the nature of the substrate, on the operating temperature, and on the final total $CH_3SO_3H/H_2O$ molar ratio present at the end of the reaction. This ratio is between approximately 2 and 6, and preferably between about 3 and 5, by operating on the various relevant parameters.

Reaction times between approximately 30 minutes and 4 hours have been demonstrated to be operative.

The separation of the N-amidic heteroatom containing heterocyclic (poly)peroxyacid of formula (I) is carried out according to per se conventional methods such as the filtration of the solid precipitate, obtained after the treatment of the reaction mixture with a solution of ammonium sulfate, or by solvent extraction, etc.

The N-amidic heteroatom-containing hetero (poly)-peroxyacids having the above formula (I) are thus obtained as crystalline solids.

The peroxycarboxylic acid products having formula (I) are solid at room temperature. According to the present invention, they may be used in formulations of detergent compositions, e.g., granular formulations, as bleaching agents in solution over a wide temperature range, for example between about 20° and about 90° C.

Therefore, the N-amidic heteroatom-containing heterocyclic peroxyacids of the presention invention may be used as bleaching agents directly alone, separately from the detergent composition, or, preferably, combined and incorporated into the conventional detergent compositions which operate over a temperature range as defined above, and comprising other components and/or additives, such as, for example, builders, surfactants, soaps, zeolites, hydrotropic agents, corrosion inhibitors, enzymes, optical bleaches, stabilizers, other bleaching compounds, etc.

Preferably, the operating temperature is between room temperature and about 65° C.

The preparation processes and the use of the compositions as well as their formulations are included within the scope of the present invention.

The peroxyacids of formula (I) of the present invention may be used in combination with solid or liquid detergent compositions, and/or in the presence of other peroxydic bleaching compounds.

Finally, the hetero-cyclic peroxyacids having the N-amidic heteroatom of the present invention are compatible with phlegmatization according to conventional methods.

The present invention is further disclosed in still greater detail in the following examples, which are supplied for purely illustrative and not limiting purposes.

The products prepared in the examples were characterized by elemental analysis, by determining their content of active oxygen (by iodometric titration), and by using Fourier Transform Infrared Spectroscopy (FT-IR).

EXAMPLE 1

11 g of methane-sulphonic acid (0.114 moles) and 2 g of N-acetyl-4-piperidinecarboxylic acid (0.0116 moles) were introduced into a beaker equipped with a stirrer, thermometer and an outer bath. The mixture was stirred at 20°-25° C. up to complete solubility. The temperature was then lowered to 5° C. and 2 g of $H_2O_2$ at 70% (0.0412 moles) were slowly introduced, and under stirring, so that the temperature was maintained at about 15° C.

The stirring was then continued for 30 minutes at 15°-20° C.

At the end, the reaction mixture was poured into 30 ml of $(NH_4)_2SO_4$ at 20% maintained under stirring at 5° C. and the resulting solution was extracted with $CH_2Cl_2$ (8×30 ml). The organic extract was washed with 30 ml of $(NH_4)_2SO_4$ at 40%, dried over anhydrous $Na_2SO_4$, filtered, and evaporated at 30° C. under vacuum.

1.1 g of crystalline, essentially pure N-acetyl-4-piperidinepercarboxylic acid were obtained.

Yield: 50%.

Elemental Analysis: Computed for $C_8H_{13}O_4N$: C=51.33%; H=7.0%; N=7.48%; O (active)=8.54%. Found: C=51.10%; H=6.97%; N=7.39%; O (active)=8.53%.

Melting point: 98° C. (with decomposition).

EXAMPLE 2

3 g of N-decanoyl-4-piperidinecarboxylic acid (0.106 moles) were completely dissolved at 25° C. into 14 g of methanesulphonic acid (0.146 moles).

By following the procedures of Example 1, 2 g of $H_2O_2$ at 85% (0.05 moles) were then added in such a way as not to exceed 15° C. The stirring was then continued at a temperature of 15°-20° for 1.5 hours. At the end, the reaction mixture was poured into 40 ml of $(NH_4)SO_4$ at 20% maintained under stirring at 5° C. It was then treated according to Example 1 by extracting the solution with $CH_2Cl_2$ (3×40 ml). After evaporation of the organic extract, 2.8 g of crystalline, essentially pure N-decanoyl-4-piperidinepercarboxylic acid were obtained.

Yield: 88%.

Elemental Analysis: Computed for $C_{16}H_{29}O_4N$: C=64.18%; H=9.76%; N=4.76%; O (active)=5.34%. Found: C=64.23%; H=9.89%; N=4.66%; O (active)=5.33%.

Melting point: 52° C. (with decomposition).

EXAMPLE 3

6 g of N, N'-adipoyl-bis (4-piperidinecarboxylic) acid (0.0163 moles) were suspended, under stirring, into 42 g of methanesulphonic acid (0.437 moles).

6 g of $H_2O_2$ at 85% (0.15 moles) were added to this cloudy solution, maintained at 5° C. so as to not exceed 15° C. The stirring was then continued at a temperature of 15°-20° C. for 2.5 hours.

At the end, the reaction mixture was poured into 150 ml of $(NH_4)_2SO_4$ at 10% maintained under stirring at 5° C. After 30 minutes, the solid product was filtered over a porous septum under vacuum, washed with ice water (3×30 ml), then with tetrahydrofurane (30 ml), and then with ethyl ether (2×30 ml). It then was dried under vacuum and over a $CaCl_2$ drier for 2 hours at room temperature.

6.2 g of N, N'-adipoyl-bis (4-piperidine-percarboxylic acid) were obtained.

Yield: 94%.

Elemental Analysis: Computed for $C_{18}H_{28}O_8N$: C=53.99%; H=7.05%; N=6.99%; O (active)=7.99%. Found: C=53.32%; H=7.19%; N=6.64%; O (active)=7.98%.

Melting point: 141° C. (with decomposition).

EXAMPLE 4

4.5 g of N-decanoyl-3-piperidinecarboxylic acid (0.0158 moles) are completely dissolved into 21 g of methanesulphonic acid (0.218 moles).

Following the procedures of Example 1, 3 g of $H_2O_2$ at 85% (0.075 moles) are added to this mixture so that the temperature was maintained at about 15° C. The stirring was then continued at a temperature of 15°-20° C. for 1.5 hours. At the end, the reaction mixture was poured into 50 ml of $(NH_4)_2SO_4$ at 20% maintained under stirring at 5° C. and then treated as in Example 1 by extracting the solution with $CH_2Cl_2$ (3×50 ml).

After evaporation of the organic extract, 3.9 g crystalline, pure at 99%. N-decanoyl-3-piperidine-percarboxylic acid were obtained.

Yield: 80%.

Elemental Analysis: Computed for $C_{16}H_{29}O_4N$: C=64.18%; H=9.76%; N=4.67%; O (active)=5.34%. Found: C=64.18%; H=9.84%; N=4.65%; O (active)=5.28%.

Melting point: 48° C. (with decomposition).

EXAMPLE 5

By operating according to the process conditions of Example 1, 4.3 g of $H_2O_2$ at 85% (0.107 moles) were added to a mixture of 4 g of N, N'-succinyl-(3-piperidinecarboxylic) acid (0.018 moles) and 29 g of methanesulphonic acid, so that the temperature was maintained at about 15° C. The stirring was then continued at the temperature of 15°-20° C. for 2.5 hours. At the end, the reaction mixture was poured into 100 ml of $(NH_4)_2SO_4$ at 20% maintained under stirring at 5° C.

After 30 minutes, the thus-formed solid product was filtered and then the procedure of Example 3 was followed.

3.8 g of crystalline, essentially pure N, N'-succinyl-bis (3-piperidinepercarboxylic) acid were obtained.

Yield: 86%.

Elemental Analysis: Computed for $C_{16}H_{24}O_8N_2$: C=51.6%; H=6.49%; N=7.25%; O (active)=8.59%. Found: C=51.42%; H=6.52%; N=7.31%; O (active)=8.58%.

The product decomposes at about 130° C. without melting.

EXAMPLE 6

Application Example

Bleaching tests were carried out with the novel heterocyclic peroxyacids having the N-amidic heteroatom according to this invention, as reported in Tables 1 and 2 below, at an alkaline pH (Table 1) and at an acid pH (Table 2), in comparison to:

H 48 (Mg salt of monoperphthalic acid), a commercial peroxyacid known in the detergent field, manufactured by INTEROX Chemical, Ltd., London, U.K. (Tables 1 and 2).

All tests were carried out at a constant temperature of 60° C., with an initial concentration of total active oxygen in the bleaching solution equal for all products, and equal to 200 mg/l.

Process

For each test, 500 ml of deionized water, contained inside a 1,000 ml flask equipped with a condenser, was heated to a temperature of 60° C. and adjusted to a pH value of 9.5 (with Na OH) (Table 1) and to a pH value of 2-3 (with a few drops of dilute $H_2SO_4$) (Table 2). The bleaching product was then added under stirring with the amounts thereof being added as shown in the following Tables, and immediately thereafter two cotton specimens of 10 cm×10 cm stained with standard stains of red wine at EMPA INSTITUTE of St. Gallen (Switzerland), and marked by "EMPA 114" mark, were added.

The system was subsequently kept stirred for 60 minutes and, at the end of this time, the specimens, rinsed under running water, were dried and ironed and were then submitted for evaluation of the bleaching effect by means of measurements of degree of whiteness by reflectometry. The results are reported in the following Tables 1 and 2, wherein the data are expressed as Bleaching %, defined as:

$$\text{Bleaching \%} = \frac{A - B}{C - B} \times 100$$

A=degree of whiteness (%) of the specimen bleached after the test;

B=degree of whiteness (%) of the specimen before the test;

C=degree of whiteness (%) of the completely bleached specimen, and wherein the degrees of whiteness were measured by means of an Elrepho Zeiss reflectometer, assuming MgO=100% as the white reference, and using filter N.6 ($\lambda$=4.64 mm).

The data in Table 1 (tests at alkaline pH), evidence that the novel peroxy acids of the present invention have a bleaching power comparable with that of H 48.

TABLE 1

| | Tests at Alkaline pH (9.5) | | |
|---|---|---|---|
| Compound | Amounts used in the test (grams) | Initial concentration of total active oxygen (mg/l) | Bleaching (%) |
| Example 3 (titer = 7.98% of active oxygen) | 1.25 | 200 | 81.8 |
| Example 2 (titer = 5.33% of active oxygen) | 1.88 | 200 | 75.4 |
| H 48 (titer = 5.5% of active oxygen) | 1.86 | 200 | 80.0 |

Likewise, the results, expressed as Bleaching %, as reported in Table 2, show that these products have a bleaching power in an acid solution particularly high and indeed significantly higher than the bleaching power of H 48.

These results are particularly surprising considering that peroxyacid compounds generally show a bleaching activity that is very modest and sometimes negligible at acid pH.

TABLE 2

| | Tests at Acid pH (2-3) | | |
|---|---|---|---|
| Compound | Amounts used in the test (grams) | Initial concentration of total active oxygen (mg/l) | Bleaching (%) |
| Example 2 (titer = 5.33% of active oxygen) | 1.88 | 200 | 70.3 |
| H 48 (titer = 5.5% of active oxygen) | 1.86 | 200 | 60.0 |

What is claimed is:

1. Heterocyclic (poly)-percarboxylic acid having an amidic nitrogen heteroatom in the ring, and having the formula:

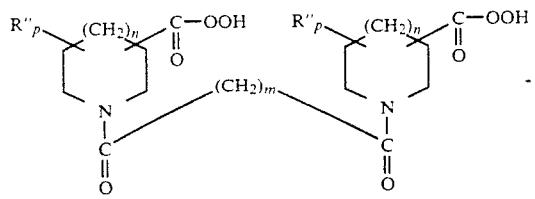

wherein:
m is an integer from 1 to 12;
n is 0 or an integer selected from 1 and 2;
p is an integer from 1 to 3.
R" is selected from H, F, Cl, $NO_2$ and;
the carboxylic group (COOH);
the ($C_1$–$C_5$) alkoxy groups;
the alkyl, cycloalkyl, alkylaryl and arylalkyl groups, containing up to 10 carbon atoms and optionally bearing a substituent group selected from F, Cl, $NO_2$, the carboxylic group and the ($C_1$–$C_5$) alkoxy groups.

2. Heterocyclic (poly)-percarboxylic acid having an amidic nitrogen heteroatom in the ring, and having the formula:

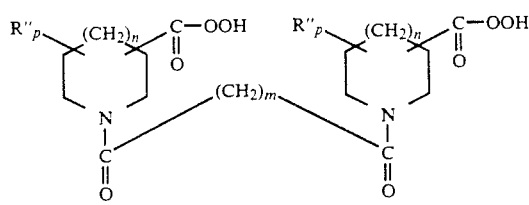

wherein:
m is an integer from 1 to 12;
n is 1;
p is an integer from 1 to 3.
R" is selected from H, F, Cl, $NO_2$ and;
the carboxylic group (COOH);
the ($C_1$–$C_5$) alkoxy groups;
the alkyl, cycloalkyl, alkylaryl and arylalkyl groups, containing up to 10 carbon atoms and optionally bearing a substituent group selected from F, Cl, $NO_2$, the carboxylic group and the ($C_1$–$C_5$) alkoxy groups.

3. The acid of claim 1, wherein R" is the carboxylic (—COOH) group and wherein said COOH group is in a non-ortho position, with respect to said amidic nitrogen heteroatom.

4. The compound: N,N'-adipoyl-bis (4-piperidinepercarboxylic) acid.

5. The compound: N,N'-succinyl-bis (3-piperidinepercarboxylic) acid.

* * * * *